US00PP31890P2

(12) United States Plant Patent
Jones

(10) Patent No.: US PP31,890 P2
(45) Date of Patent: Jun. 16, 2020

(54) ***GAILLARDIA* 'GHOMO07-0'**

(50) Latin Name: *Gaillardia grandiflora*
Varietal Denomination: GHOMO07-0

(71) Applicant: Steve Jones, Santa Monica, CA (US)

(72) Inventor: Steve Jones, Santa Monica, CA (US)

( * ) Notice: Subject to any disclaimer, the term of this patent is extended or adjusted under 35 U.S.C. 154(b) by 0 days.

(21) Appl. No.: 16/602,147

(22) Filed: Aug. 14, 2019

(51) Int. Cl.
*A01H 5/02* (2018.01)
*A01H 6/14* (2018.01)

(52) U.S. Cl.
USPC ..... Plt./431

(58) Field of Classification Search
USPC ..... Plt./431
CPC ..... A01H 5/02; A01H 6/14
See application file for complete search history.

*Primary Examiner* — Annette H Para
(74) *Attorney, Agent, or Firm* — Cassandra Bright

(57) ABSTRACT

A new and distinct *Gaillardia* cultivar named 'GHOMO07-0' is disclosed, characterized by unique large, bright yellow flowers. Plants have a tight, round compact habit. The new variety is a *Gaillardia*, normally produced as an outdoor garden or container plant.

2 Drawing Sheets

Latin name of the genus and species: *Gaillardia grandiflora.*

Variety denomination: 'GHOMO07-0'.

BACKGROUND OF THE INVENTION

The new *Gaillardia* cultivar is a product of open pollination by the inventor, Steve Jones, at a commercial nursery in Santa Paula, Calif. The open pollination was made in April 2016.

Various unnamed, unpatented proprietary *Gaillardia grandiflora* varieties were planted in open-pollination crossing blocks and the resulting seed bulk collected. Parent varieties are unidentified. The new variety was selected in September 2016 by the inventor in a group of seedlings at the same nursey in Santa Paula, Calif.

Asexual reproduction of the new cultivar 'GHOMO07-0' by terminal vegetative cuttings was first performed at a greenhouse in Santa Paula, Calif. in October 2016, and has shown that the unique features of this cultivar are stable and reproduced true to type in successive generations.

SUMMARY OF THE INVENTION

The cultivar 'GHOMO07-0' has not been observed under all possible environmental conditions. The phenotype may vary somewhat with variations in environment such as temperature, day length, and light intensity, without, however, any variance in genotype.

The following traits have been repeatedly observed and are determined to be the unique characteristics of 'GHOMO07-0' These characteristics in combination distinguish 'GHOMO07-0' as a new and distinct *Gaillardia* cultivar:

1. Unique bright yellow flowers.
2. Large flowers.
3. Tight, round plant habit.

PARENT COMPARISON

The parent varieties cannot be identified.

COMMERCIAL COMPARISON

Plants of the new cultivar 'GHOMO07-0' are comparable to the variety *Gaillardia* 'Oranges and Lemons', U.S. Plant Pat. No. 17,092. The two *Gaillardia* varieties are similar in most horticultural characteristics, however, the new variety 'GHOMO07-0' differs in the following:

1. Plants of 'GHOMO07-0' are on average at least 30% shorter, than plants of 'Oranges and Lemons'.
2. Plants of 'GHOMO07-0' are much more compact than plants of 'Oranges and Lemons'.
3. Flower color of 'GHOMO07-0' is bright yellow, compared to the bi-color orange-yellow flower of 'Oranges and Lemons'.

BRIEF DESCRIPTION OF THE PHOTOGRAPHS

Figure 1:
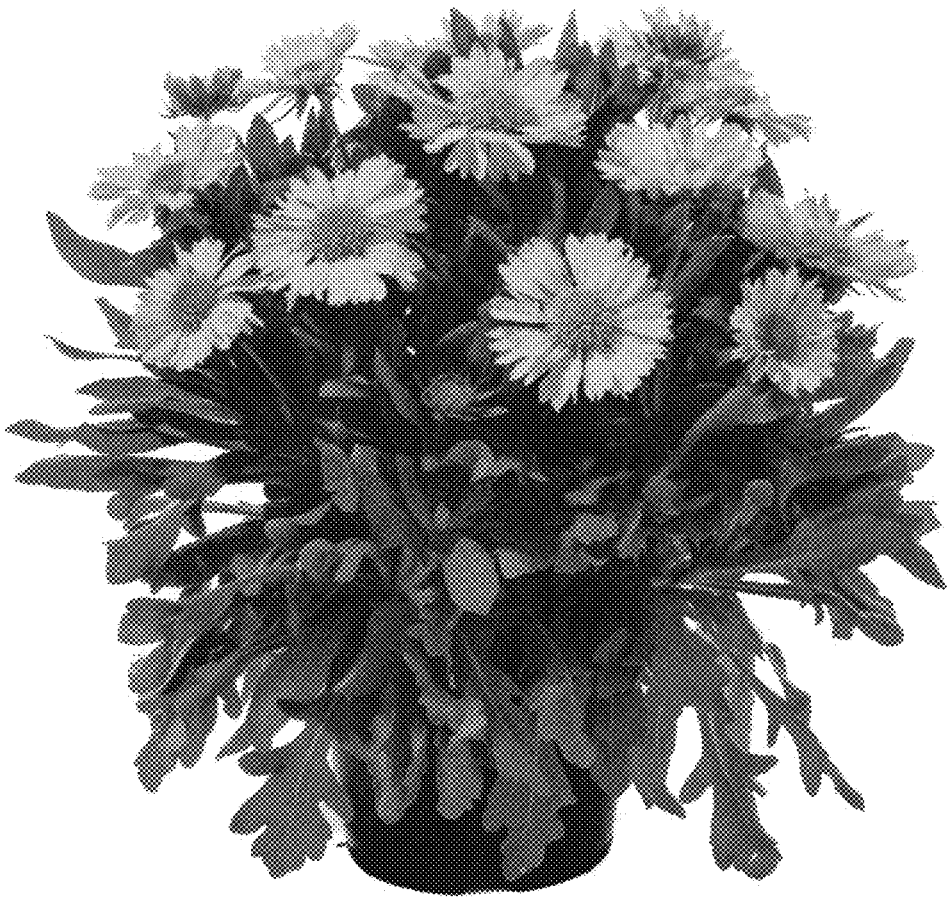

The accompanying photograph in FIG. 1 illustrates in full color a typical plant of 'GHOMO07-0' grown in a nursery in a 1 gallon pot. Age of the plant photographed is approximately 8 months from a rooted cutting.

Figure 2:
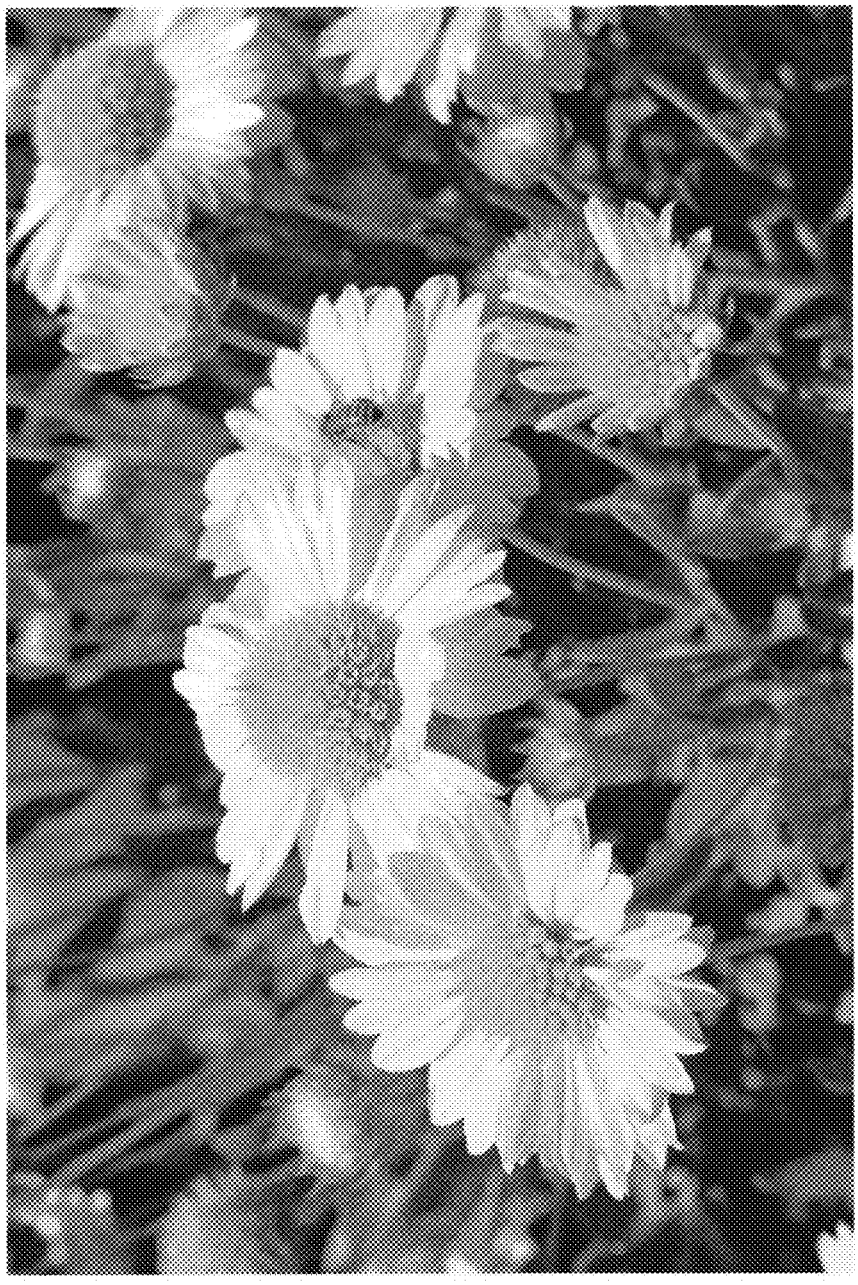

FIG. 2 illustrates in full color a close up of typical blooms of 'GHOMO07-0'. The photographs were taken using conventional techniques and although colors may appear different from actual colors due to light reflectance it is as accurate as possible by conventional photographic techniques.

DETAILED BOTANICAL DESCRIPTION

In the following description, color references are made to The Royal Horticultural Society Colour Chart 2007 except where general terms of ordinary dictionary significance are used. The following observations and measurements describe 'GHOMO07-0' plants grown outdoors during Spring in Santa Paula, Calif. The growing temperature ranged from 8° C. to 25° C. during the day and from 3° C. to 12° C. during the night. General light conditions are bright, normal sunlight. Measurements and numerical values represent averages of typical plant types. Plants are approximately 120 days old from a rooted cutting.

Botanical classification: *Gaillardia grandiflora* 'GHOMO07-0'.

PROPAGATION

Time to initiate roots: About 3-4 days summer, 4-5 days winter.

Root description: Fleshy, white, branching.

PLANT

Growth habit: Upright.

Pot size of plant described: 40 cm.

Height: 30 cm to foliar plane. 40 cm to top of highest inflorescence.

Plant spread: 60 cm.

Growth rate: Rapid.

Branching characteristics: Moderately well branched.

Length of primary lateral branches: 10 to 14 cm.

Quantity of primary lateral branches: 15 to 18, from 3 rooted cuttings.

Characteristics of primary lateral branches:

*Form.*—Round, with ridges.

*Diameter.*—0.4 cm.

*Color.*—RHS Yellow-Green 145B.

*Texture.*—Moderately villous. Hairs approximately 0.2 cm, colored RHS White 155D.

*Strength.*—Strong.

Internodes length: Average range 1.5 to 3.0 cm.

FOLIAGE

Leaf:

*Shape.*—Narrow spatulate.

*Quantity.*—Approximately 16 to 24 per branch.

*Average length.*—10 cm.

*Average width.*—1.5 to 2.0 cm.

*Apex.*—Acute.

*Base.*—Attenuate.

*Margin.*—Irregularly dentate.

*Texture of top surface.*—Pubescent, rough.

*Texture of bottom surface.*—Pubescent, rough.

*Aspect.*—Slightly undulating and reflexed down.

*Color.*—Young foliage upper side: RHS Green 137C. Young foliage under side: RHS Green 137D. Mature foliage upper side: RHS Green 138A. Mature foliage under side: RHS Green 138A.

*Venation.*—Type: Pinnate. Venation color upper side: RHS Yellow-Green 144C. Venation color under side: RHS Yellow-Green 145B.

*Petiole.*—Absent.

FLOWER

Natural flowering season: Spring and Summer.

Inflorescence and flower type and habit: Terminal capitulate.

Rate of flower opening: 3 to 5 days from bud to fully opened flower.

Flower longevity on plant: 7-10 days depending upon environmental conditions.

Persistent or self-cleaning: Self-cleaning ray florets, disc florets persistent.

Flower size:

*Diameter of entire flower.*—Approximately 6 to 7.5 cm.

*Depth of flower.*—Approximately 2.0 cm.

*Disc diameter.*—Approximately 3.5 cm.

*Receptacle shape.*—Disc florets very tightly held to receptacle. Dome shaped, approximately 0.6 mm in height, and 9 mm in diameter. Colored White 155A.

*Quantity of inflorescences per lateral stem.*—7-15.

Bud:

*Shape.*—Flattened globular.

*Length.*—1.2 cm.

*Diameter.*—1.8 cm.

*Color.*—Near RHS Green 138B.

Ray florets:

*Quantity.*—Average 25.

*Arrangement.*—Rotate in 2 whorls.

*Length.*—3.0 to 3.5 cm.

*Width.*—1.5 cm.

*Shape.*—Overall deltate, with 3 apical lobes. Lobes lanceolate, approximately 0.4 cm width and 0.5 cm depth.

*Apex.*—Each lobe apex acute.

*Base.*—Attenuate.

*Margin.*—Entire.

*Texture, upper and lower surfaces.*—Glabrous.

Color:

*When opening.*—Upper Surface: RHS Yellow-Orange 14A, base Yellow 13B. Lower Surface: RHS Yellow 13A, base Yellow 12B.

*Fully opened.*—Upper Surface: RHS Yellow 13A. Lower Surface: RHS Yellow 12A.

*Fading with age.*—Upper Surface: RHS Yellow 13A. Lower Surface: RHS Yellow 13B.

Disc florets:

*Quantity.*—Approximately 150.

*Length.*—0.9 cm.

*Width.*—Base 0.2 to 0.3 cm, apex flaring to 0.4 cm.

*Shape.*—Cylindric.

*Apex.*—Opening to jagged acute fringes.

*Base.*—Fused.

*Margin.*—Entire.

*Texture, all surfaces.*—Glabrous.

*Color.*—When opening: All visible surfaces: RHS Green-Yellow 1C. Apex Yellow 12A. Fully opened: All visible surfaces: RHS Green-Yellow 1D. Apex Yellow-Orange 15A. Fading with Age: All visible surfaces: RHS Green-Yellow 1D. Apex Yellow-Orange 17A.

Phyllaries/involucral bracts:

*Quantity.*—35 to 40.

*Length.*—10 to 11 mm.

*Width.*—3 mm.

*Shape (overall).*—Narrow deltate.

*Apex.*—Narrowly acute.

*Base.*—Cuneate.

*Texture.*—Pubescent all surfaces.

*Margin.*—Entire, slightly villous.

*Color.*—All Surfaces near RHS Green 137C.

Peduncles:

*Length.*—Average range 10 to 12 cm.

*Diameter.*—0.2 cm.

*Angle.*—About 10° to the lateral branch.

*Strength.*—Strong, flexible.

*Texture.*—Pubescent.

*Color.*—RHS Green 138B.

Fragrance: Mild fresh scent.

REPRODUCTIVE ORGANS

Ray florets: No reproductive organs observed.

Disc florets:

Stamens:

*Number.*—6.

*Length.*—About 2 mm.

*Color.*—Near White 155D.

Anthers:

*Shape.*—Linear.

*Length.*—Approximately 1 mm.

*Color.*—RHS Yellow-Orange 22A.

*Pollen.*—Color: RHS Yellow 13A. Quantity: Scant.

Pistil:

*Number.*—1.

*Length.*—1.1 cm. Style: Length: 5 mm. Color: RHS White 155D. Stigma: Shape: Bifid, curled outward. Color: RHS Yellow 13B.

*Ovary color.*—RHS Yellow-Green Group 144D.

OTHER CHARACTERISTICS

Seeds and fruits: Seed set not observed to date.

Disease/pest resistance: Neither resistance nor susceptibility to disease or pests has been observed in this variety. Typical pests of *Gaillardia* include whitefly, aphid and leafminor. Typical diseases include Thielaviopsis, Botrytis, Rhizoctonia and Pythium.

Temperature tolerance: USDA Zones 5 through 10.

What is claimed is:

1. A new and distinct cultivar of *Gaillardia* plant named 'GHOMO07-0' as herein illustrated and described.

* * * * *